United States Patent [19]

Ollivier et al.

[11] Patent Number: 5,362,151
[45] Date of Patent: Nov. 8, 1994

[54] DEVICE FOR MEASURING THERMAL EXPANSION

[75] Inventors: Jean-Francois Ollivier, Merdrignac; Said Lalaouna, La Ferte Bernard; Manuel Penha, Le Mans, all of France

[73] Assignee: Framatome Connectors International, Paris La Defense Cedex, France

[21] Appl. No.: 35,752

[22] Filed: Mar. 24, 1993

[30] Foreign Application Priority Data

Mar. 26, 1992 [FR] France .................................. 92 03659

[51] Int. Cl.$^5$ ............................................. G01N 25/16
[52] U.S. Cl. ...................................... 374/55; 356/387; 374/56; 374/6
[58] Field of Search .......................... 374/55, 56, 6, 7; 356/387

[56] References Cited

U.S. PATENT DOCUMENTS

| | | | |
|---|---|---|---|
| 2,351,572 | 6/1944 | Kingston | 374/55 |
| 2,546,796 | 3/1951 | Swanson et al. | 374/56 |
| 3,877,290 | 4/1975 | Cheng | 374/56 |
| 4,923,307 | 5/1990 | Gilmore et al. | 374/56 |
| 4,976,549 | 12/1990 | Khan | 374/56 |
| 4,989,980 | 2/1991 | Berg | 374/55 |

FOREIGN PATENT DOCUMENTS

| | | | |
|---|---|---|---|
| 0929515 | 6/1955 | Germany | 374/55 |
| 0386287 | 6/1973 | U.S.S.R. | 374/56 |

OTHER PUBLICATIONS

Ivlev et al., "Dilatometer using photoelectric recording of elongation," Ind. Lab. (USA), vol. 37, No. 12 (Dec. 1971).

Lloyd, L. T., "Recording Quartz Differential Dilatometer," ANL-5372 (Argonne National Laboratory), pp. 7-13, 21, 22, 21, 33, 34, 36, 40 (Jul. 1959).

Primary Examiner—Diego F. F. Gutierrez
Attorney, Agent, or Firm—Wegner, Cantor, Mueller & Player

[57] ABSTRACT

A device for measuring the thermal expansion of a sample comprises a measurement radiation generator, a base member incorporating a reference groove and a furnace. The furnace has an external reference contour adapted to cooperate with the reference groove, an internal reference contour adapted to cooperate with a sample and an aperture through which the measurement radiation passes.

9 Claims, 2 Drawing Sheets

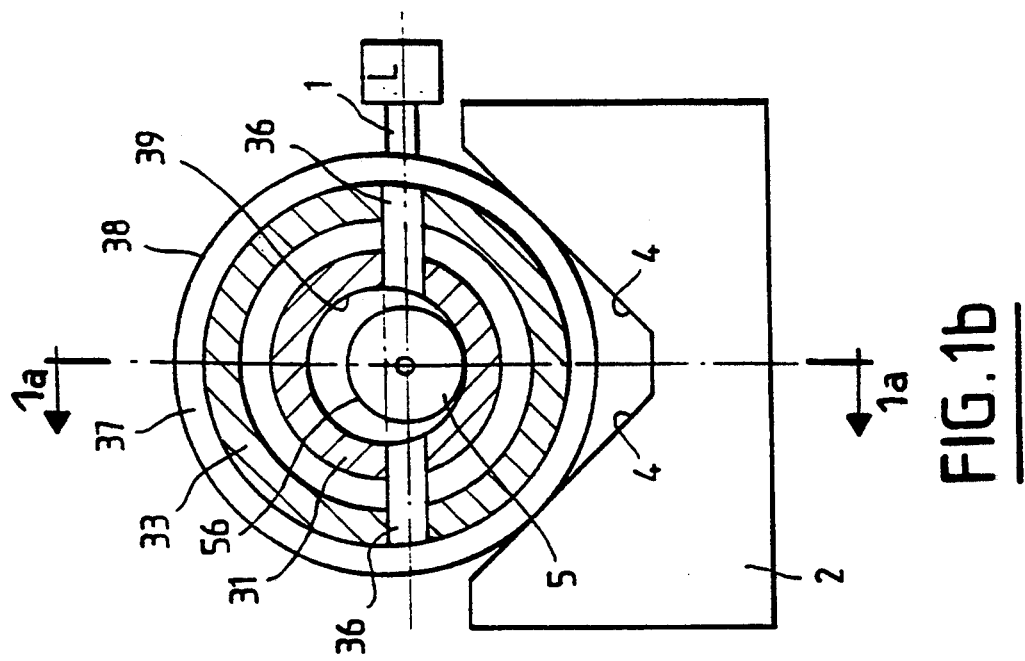
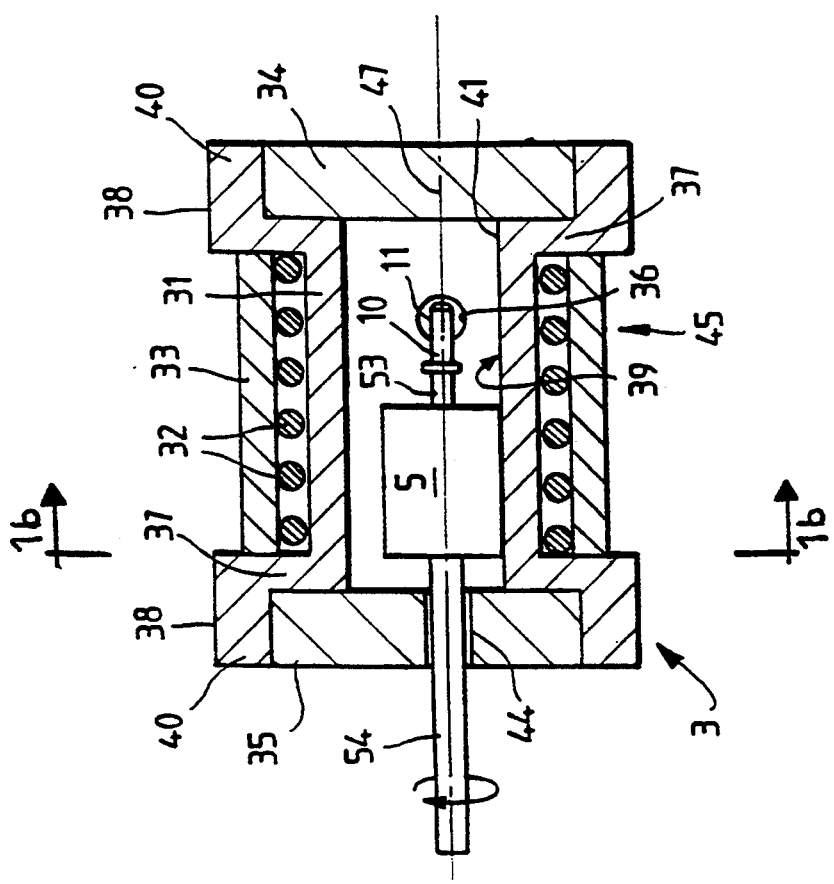
FIG. 1a
FIG. 1b

DEVICE FOR MEASURING THERMAL EXPANSION

BACKGROUND OF THE INVENTION

1. Field of the Invention

The invention concerns a device for measuring thermal expansion, in particular thermal expansion of a ferrule adapted to receive an optical fiber.

2. Description of the Prior Art

An optical fiber connector ferrule has a highly accurate cylindrical exterior contour and a highly accurate axial aperture on the ferrule axis. The aperture diameter, typically 125 microns, is matched to the exterior diameter of an optical fiber complete with its optical cladding. The exterior contour of any such ferrule must be precisely cylindrical, with an accuracy of better than 1 micron. The nominal diameter of the exterior contour being 2 500 microns for a standard optical fiber connector ferrule, the accuracy required means that thermal expansion measurements have to be carried out to determine the behavior of the component.

In the case of a plastics material ferrule, measuring the diameter using mechanical feelers has the drawback of being poorly reproducible since the impact of the feelers on the surface of the ferrule is likely to crush the latter by an amount in the order of a few microns, so that the measurement is insufficiently accurate.

It is known to measure the size of a sample using a laser beam and a base member incorporating a reference groove, usually of V-shape, in which the sample to be measured is placed.

An object of the present invention is a thermal expansion measurement device offering high accuracy compatible with that required for measurement of optical fiber connector ferrules.

SUMMARY OF THE INVENTION

In a first aspect the invention consists in a device for measuring the thermal expansion of a sample comprising:

means for generating measurement radiation a base member incorporating a reference groove, and a furnace having an external reference contour adapted to cooperate with said reference groove, an internal reference contour adapted to cooperate with a sample and an aperture through which said measurement radiation passes.

The measurement equipment is simplified and heating of the base member is avoided by placing the sample to be measured inside a precision component which also constitutes a furnace for heating the sample to be measured.

The reference groove is advantageously V-shape, presenting bifurcated arms with surfaces for supporting the furnace.

In one particularly advantageous embodiment at least one reference contour is cylindrical. Two generatrices of the exterior cylindrical contour of the furnace are then in contact with the arm surfaces of the V-shape groove in the reference member and the axis of the furnace and the laser beam produced by the measurement bench are very accurately orthogonal. Therefore, the contact between the arms and the furnace is a straight line contact. Moreover, a cylindrical internal reference contour simplifies positioning of the sample or of a cylindrical sample-holder which rests under its own weight with one generatrix on the lowest generatrix of the internal reference contour of the furnace. The contact between the holder and the inside surface of the furnace is a single straight line contact.

In one particularly advantageous embodiment the furnace has first and second end portions, each of which has an external reference contour portion, and a central portion of smaller cross-section than the external reference contour and in which a heating element is disposed. This structure, along with other aspects of the invention limits the heating effect to the portion of the furnace directly around the sample to be measured which avoids significant transmission of heat to the base member.

Another problem with cylindrical parts is that a ferrule may have a number of non-circularity, misalignment, etc defects distributed around all of its contour. Its positioning within the interior reference contour along a generatrix of the cylinder, in the manner described hereinabove, is in practise conditioned by the aforementioned defects and can therefore falsify the measurement result, in particular because the ferrule is not necessarily precisely perpendicular to the direction of the light beam. In this case the measured diameter is greater than the actual diameter and the expansion measurement cannot be carried out simultaneously with a highly accurate diameter measurement.

With the aim of avoiding this drawback the measurement device in accordance with the invention comprises a sample-holder having an external reference profile adapted to cooperate with said internal reference contour and a reference member adapted to receive the sample. This prevents contact between the sample and the internal reference contour which eliminates or at least goes a long way towards eliminating the aforementioned drawbacks.

The external reference profile is advantageously cylindrical and has a cross-section smaller than that of the internal reference contour.

It is advantageous to dispose the measurement beam aperture below the longitudinal axis of the furnace to reduce convection of air within the furnace.

In a second aspect the invention consists in a method of measuring the thermal expansion of a sample utilizing a device in accordance with the first aspect of the invention as defined hereinabove, said method comprising the following steps:

disposing said external reference contour of said furnace in said reference groove of said base member, disposing a sample in said furnace so that it is positioned accurately relative to said internal reference contour, and heating said furnace and measuring a dimension of said sample at at least one temperature and in at least one position of said sample.

Other features and advantages of the invention will be better understood from the following description given by way of non-limiting example with reference to the appended drawings.

BRIEF DESCRIPTION OF THE DRAWINGS

FIG. 1a is a view in longitudinal cress-section as indicated by arrows 1a—1a in FIG. 1b, showing a furnace in accordance with the invention and a sample.

FIG. 1b is a cross-section, as indicated by arrows 1b—1b in FIG. 1a, of the furnace disposed in a base member.

DETAILED DESCRIPTION OF THE INVENTION

Figure 2C:
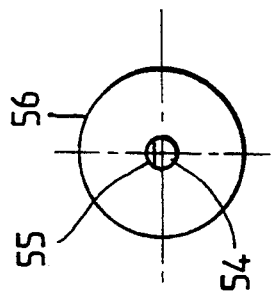
FIGS. 2a, 2b, and 2c are right side elevation, longitudinal cross-section, and left side elevation views, respectively, of a sample-holder of one embodiment of the invention.

Referring to FIGS. 1a and 1b, a base member 2 incorporates a V-shape groove in which is disposed a furnace 3, with bifurcated arms of the V-shape groove presenting surfaces 4 (FIG. 1b) for supporting engagement with having an external cylindrical contour 38 machined to an accuracy of better than 1 micron. The thermally conductive material body of the furnace 3 has a central cylindrical cross-section 31 whose inside surface has a cylindrical reference contour 39 machined to an accuracy in the order of 1 micron. The contour 39 is coaxial with the contour 38 to within an accuracy of better than 1 micron. Portions of the body of the furnace 3 are thermally insulated. The cylindrical contour 38 at each end of the furnace 3 has a diameter greater than that of central portion 31 and, thus, defines an annular groove 45. A heater element 32 and surrounding thermally insulative cylindrical member 33 are disposed within the bounds of annular groove 45. Thermally insulative members 34, 35 are placed at the longitudinal ends of the furnace 3. One of them (35) is removable and has an aperture 44 to enable a sample-holder 5 to be manipulated (see below).

The sample 10 to be measured is positioned so that it intercepts a light beam 1 on the axis of a transverse aperture 36 of the furnace and passing through the central portion 31, the heating element 32 and the cylindrical insulation 33. The laser beam emitted from box L (FIG. 1b) may be produced by a known "LASER-MIKE" dimensional measurement bench marketed by the company O. R. C. of 77680 ROISSY EN BRIE, FRANCE, specifically the 183-100 model including a helium-neon laser producing a laser beam with a wavelength of 632.8 nm from which a "laser curtain" is formed by a rotating mirror and a collimator lens (not shown). The beam 1 is perpendicular to the longitudinal axis of the reference groove arm surfaces 4. The insertion of a sample 10 to be measured produces a shadow which generates an electrical signal whose duration is proportional to the size of the object to be measured and dependent on the speed at which the laser beam 1 is scanned. The electrical signal is decoded to obtain the size of the sample, in this instance the diameter, with a resolution in the order of 0.2 microns. Thermal expansion measurements are carried out in this way and during such measurements the temperature of the oven is monitored using a probe (not shown) situated on axis 47.

Note that the axis of the aperture 36 is slightly below the longitudinal axis of the furnace in order to prevent convection currents within the latter producing non-homogeneous heating. Also, the provision of the thermal insulation 33, 34, 35 around the central portion of the furnace around the sample prevents significant heating of the external contour 38 which would otherwise compromise the accuracy of the measurement, in particular through localized heating of the base member 2.

Figure 2B:
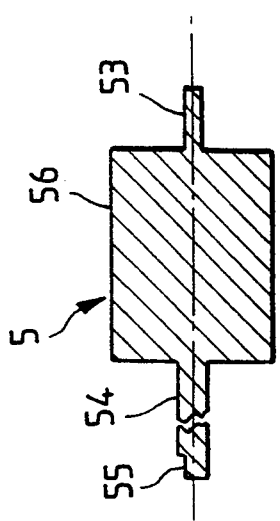
Figure 2A:
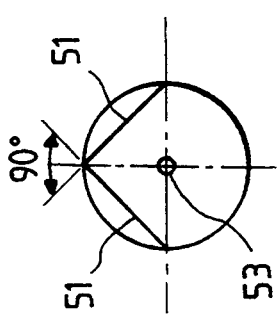
Figure 3:
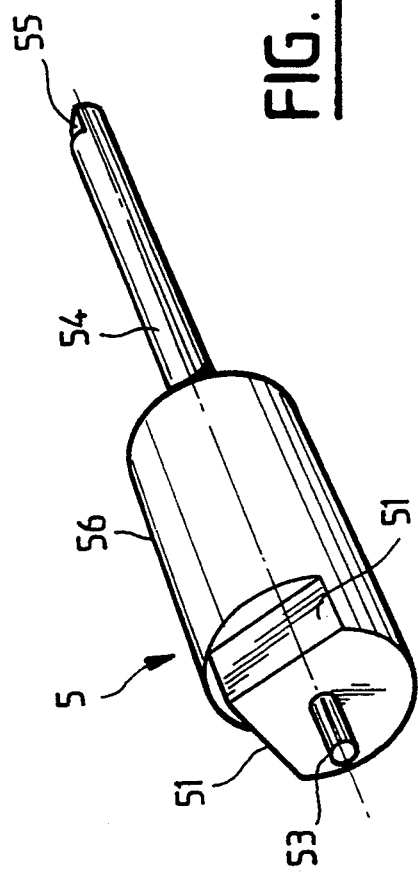
FIG. 3 is an isometric view of the sample-holder of FIGS. 2a—2c.

Referring to FIGS. 2a through 2c and 3, a sample-holder 5 has at one end a precisely machined spindle 53 which is coaxial with its cylindrical exterior contour 56 to within an accuracy of better than 1 micron. The sample 10 can be moved (by hand or using an automatic mechanism) by means of a cylindrical peg 54 at the other end of the sample-holder 5 which has a notched end 55 and which passes through the aperture 44 in the insulative cover 35. The notch 55 provides a visual angular position indication.

With particular reference to FIG. 1b, the sample-holder 5 rests under its own weight with one generatrix in contact with the lowest generatrix 41 of the internal reference contour 39. The central aperture has a nominal diameter of 0.9 mm for an optical fiber connector ferrule 10. It is sleeved over the end of the cylindrical portion 53 and the external contour 11 of the ferrule 10 intercepts the laser beam 1 to enable its diameter to be measured (2 500 microns for an optical fiber connector ferrule, for example).

To carry out a thermal expansion measurement the sample-holder 5 carrying a ferrule 10 to be measured is inserted into the furnace 3 which is then closed. One or more measurements are then carried out at one or more temperatures. If necessary, the sample 10 is moved inside the furnace 3 by means of the cylindrical portion 54 extending out of the furnace through the aperture 44. It is therefore possible to measure the thermal expansion of a sample and the accuracy with which it returns to its nominal size after thermal cycling.

There is claimed:

1. Device for measuring the thermal expansion of a sample having a measurement contour, said device comprising:

means for generating a curtain of measurement radiation which is useable to measure a diameter of said sample, a base member incorporating a reference groove, a furnace having an external reference contour contacting and located by said reference groove, an internal reference contour contacting and locating an external reference profile which is disposed and positioned relative to said measurement contour of said sample, an aperture through which said curtain of measurement radiation passes, and a removable member at one end of said furnace having another aperture therethrough, a sample-holder having said external reference profile and a reference member to receive said sample, said sample-holder further having an extension extending through said another aperture of said removable member to enable displacement of said sample-holder; and said reference groove, said external reference contour, said internal reference contour, said external reference profile and said measurement contour being disposed relative to one another and to said curtain of measurement radiation such that a surface of said curtain is disposed substantially perpendicular to an axis of said measurement contour.

2. Device according to claim 1 wherein said reference groove is V-shape.

3. Device according to claim 1 wherein at least one of said reference contours is cylindrical.

4. Device according to claim 1 wherein said furnace has first and second end portions, each of which presents a portion of said external reference contour, said end portions being joined by a central portion which is smaller in cross-section than said external reference contour and in which a heating element is disposed.

5. Device according to claim 1 wherein said external reference profile is cylindrical and smaller in cross-section than said internal reference contour.

6. Device according to claim 1 wherein said external reference contour and said internal reference contour of said furnace are parts of a common member constituting a furnace body.

7. Device according to claim 1 wherein a central portion of an external surface of said furnace comprises a thermally insulative material.

8. Device according to claim 1 wherein said aperture is below a longitudinal axis of said furnace.

9. An apparatus for using measuring radiation to measure dimensional change of a sample in response to thermal change applied thereto, and comprising:

a furnace having a cylindrical external reference surface defining a first longitudinal axis, a cylindrical internal reference surface defining a second longitudinal axis oriented parallel to said first longitudinal axis, and aperture means for passing said measuring radiation into said furnace;

a base member having cradle means with at least one pair of bifurcated arms for supporting and locating said cylindrical external reference surface of said furnace relative to said base member by contact therewith, and for limiting transfer of heat to said base member from said furnace by limiting said contact to straight line contact with each of said arms;

a sample holder having a cylindrical external reference surface of lesser diameter than said cylindrical internal reference surface of said furnace such that, upon insertion of said sample holder within said furnace, said external reference surface of said sample holder is in single, straight line contact only with said internal reference surface of said furnace;

said sample holder presenting a reference member with which said sample is placed in contact such that a reference axis of said sample is maintained in a particular orientation relative to said first longitudinal axis of said furnace, while preventing said sample from contacting said internal reference surface, when said sample is situated inside said furnace in preparation for said dimensional change;

means for generating a curtain of said measuring radiation and directing said curtain through said aperture means with a surface of said curtain of radiation intersected perpendicularly by said reference axis.

* * * * *